(12) United States Patent
Thiem et al.

(10) Patent No.: US 8,850,848 B2
(45) Date of Patent: Oct. 7, 2014

(54) APPARATUS FOR SECTIONING HISTOLOGICAL SAMPLES HAVING A SPIRAL-SHAPED CAPILLARY TUBE

(75) Inventors: Stefan Thiem, Heidelberg (DE); Christian Lorenz, Dielheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 168 days.

(21) Appl. No.: 13/492,241

(22) Filed: Jun. 8, 2012

(65) Prior Publication Data

US 2012/0318075 A1 Dec. 20, 2012

(30) Foreign Application Priority Data

Jun. 16, 2011 (DE) .......................... 10 2011 051 097

(51) Int. Cl.
*F25B 1/00* (2006.01)
*B01L 7/00* (2006.01)
*G01N 1/06* (2006.01)

(52) U.S. Cl.
CPC .... *B01L 7/00* (2013.01); *G01N 1/06* (2013.01)
USPC .............................................. 62/498; 62/511

(58) Field of Classification Search
CPC ........... F25B 2600/2513; F25B 41/062; F25B 2341/063; F25B 1/00; F25B 3/00; F25B 41/06; F25B 2341/06
USPC ........................................... 62/222, 498, 511
See application file for complete search history.

(56) References Cited

U.S. PATENT DOCUMENTS

| 3,191,476 | A | | 6/1965 | Mccormick et al. |
| 4,708,886 | A | * | 11/1987 | Nelson ............................ 422/72 |
| 4,794,762 | A | * | 1/1989 | Orth et al. ....................... 62/203 |
| 7,160,717 | B2 | * | 1/2007 | Everett ....................... 435/286.2 |
| 2004/0033592 | A1 | * | 2/2004 | Shin et al. .................. 435/287.2 |
| 2006/0073584 | A1 | * | 4/2006 | Sasaki et al. ............... 435/288.5 |
| 2007/0084224 | A1 | * | 4/2007 | Yuzawa et al. .................. 62/114 |
| 2007/0189925 | A1 | * | 8/2007 | Blecka et al. .................... 422/64 |
| 2008/0017559 | A1 | * | 1/2008 | Rutgers van der Loeff et al. .............................. 210/142 |
| 2009/0038416 | A1 | * | 2/2009 | Bonner ...................... 73/864.51 |
| 2009/0263290 | A1 | * | 10/2009 | Yang et al. ..................... 422/104 |
| 2009/0280572 | A1 | * | 11/2009 | Ribeiro et al. ................ 436/164 |
| 2010/0151513 | A1 | * | 6/2010 | Vom et al. .................. 435/40.52 |

FOREIGN PATENT DOCUMENTS

| DE | 94 21 559 | 3/1996 |
| EP | 1811280 | 7/2007 |
| WO | 2004/029588 | 8/2004 |

* cited by examiner

*Primary Examiner* — Mohammad M Ali
(74) *Attorney, Agent, or Firm* — Hodgson Russ, LLP

(57) ABSTRACT

The invention relates to an apparatus (10) for sectioning histological samples, which encompasses a sectioning unit (18), a sample holder (14), and a drive unit (16) for moving the sample holder (14) relative to the sectioning unit (18) in order to section the sample (12). Also provided is a cooling unit (20), for cooling at least a sub-region of the sample holder (14), which encompasses a compressor for compressing a refrigerant, a capillary tube (25) for delivering the liquefied refrigerant from the compressor (22) to the sample holder (14), and a return line (28) for returning the refrigerant from the sample holder (14) to the compressor (22). At least a sub-region (32) of the capillary tube (25) is embodied in a spiral shape.

19 Claims, 2 Drawing Sheets

APPARATUS FOR SECTIONING HISTOLOGICAL SAMPLES HAVING A SPIRAL-SHAPED CAPILLARY TUBE

CROSS REFERENCE TO RELATED APPLICATIONS

This application claims priority of German patent application number 10 2011 051 097.4 filed Jun. 16, 2011, the entire disclosure of which is incorporated by reference herein.

FIELD OF THE INVENTION

The present invention relates to an apparatus for sectioning histological samples.

BACKGROUND OF THE INVENTION

With the aid of microtomes, the histological samples taken from a patient are first embedded in paraffin and sectioned into thin sections, which are then applied onto specimen slides and, after treatment and coverslipping, delivered to a microscope for further investigation. Cryostat microtomes, which are used to section frozen samples that, for reasons of time, cannot go through the laborious preparation process for paraffin embedding. Depending on environmental conditions, however, it may also be necessary to cool the samples that are embedded in paraffin so as to prevent an unusable sectioning result due to soft paraffin.

Microtomes in which the sample holder on which the sample is mounted is arranged in a cooled chamber through which a cooled air flow is guided for cooling, are known. The cooling that occurs with these microtomes is only a relatively imprecise cooling that is often also not sufficient for sensitive samples. To avoid this, microtomes are also known in which a compression-type refrigerating machine (as known, for example, from commercially usual refrigerators) is provided, by which the sample holder is actively cooled. A microtome of this kind is known, for example, from the document WO 2004/029588 A1.

For sectioning of the sample, the sample holder is moved relative to the sectioning unit. In particular, the sample holder performs both a sectioning motion and a feed motion. As a result of the movement of the sample holder, the lines through which the refrigerant of the compression-type refrigerating machine is guided are under constant dynamic stress; especially in the case of the thin capillary tubes through which the refrigerant is delivered to the sample holder, this results in rapid material fatigue and thus in breakage of the capillary tube. The capillary tubes must therefore be replaced frequently, which is associated with corresponding labor and cost.

DE 94 21 559 U1 discloses a cryostat microtome in which the specimen holder is connected via capillary tubes to a refrigeration unit.

EP 1 811 280 A1 discloses a microtome in which the region in which the sample is microtomed is cooled.

U.S. Pat. No. 3,191,476 A discloses a microtome in which a gaseous temperature-control medium is delivered via a corrugated tube.

What is needed is an apparatus for sectioning histological samples with which the samples can be reliably cooled, and which has a long service life.

SUMMARY OF THE INVENTION

According to the present invention, at least a sub-region of the capillary tube is embodied in a spiral shape, so that it executes a resilient motion when the sample holder is moved by the drive unit in order to section the sample, with the result that the mechanical stress on the capillary tube is substantially lower. The service life of the capillary tube is thus increased, so that it requires replacement only after an appreciably larger number of sectioning operations. The spiral-shaped sub-region compensates for the motion of the sample holder while avoiding large mechanical loads on the capillary tube in that context.

The spiral-shaped sub-region of the capillary tube is, in particular, screw-shaped, for example similarly to a helical spring.

The spiral-shaped sub-region is, in particular, embodied in a helical shape and thus has a constant pitch. The spiral-shaped sub-region is thus homogeneously loaded in the context of the sectioning motion, so that stress peaks do not occur and breakage of the capillary tube is thus effectively prevented.

The spiral-shaped sub-region is, in particular, embodied in the shape of a spring element that is elastically deformed during the sectioning motion and assumes its original shape again after sectioning.

The refrigerant is, in particular, liquid when it is conveyed through the capillary tube.

The spiral-shaped sub-region of the capillary tube comprises a plurality of turns, each two adjacent turns being at a predetermined spacing from one another. This spacing ensures that the spiral-shaped sub-region can deflect without mutual interference between the turns. In an alternative embodiment, the turns can also be embodied to be immediately adjacent to one another, i.e. no spacings exist between the turns of the spiral-shaped sub-region.

In a particularly preferred embodiment, the entire capillary tube is embodied in a spiral shape, so that upon bending of the capillary tube as a result of the motion of the sample holder, the capillary tube does not break as quickly, or exhibit other mechanical damage, even with frequent load cycling.

The spiral-shaped sub-region of the capillary tube is embodied in particular in a manner curved into an arc, so that upon bending as a result of the motion of the sample holder, a relatively homogeneous distribution of the load over the capillary tube takes place, and a particularly good resilient effect of the spiral-shaped sub-region of the capillary tube occurs.

The turns of the spiral-shaped sub-region delimit an interior space, the return line preferably extending through said interior space so that on the one hand the return line is protected, and on the other hand a particularly compact construction is achieved.

The return line itself is embodied in particular as a corrugated tube and/or a corrugated hose, so that it can compensate for the motion occurring upon sectioning of the sample without the occurrence, in that context, of large loads and mechanical damage.

In a particularly preferred embodiment, a further delivery line is provided in order to deliver gaseous refrigerants to the sample holder, said further delivery line also extending, in particular, through the interior space of the spiral-shaped sub-region of the capillary tube so that on the one hand said further delivery line is also protected, and on the other hand a particularly compact construction is achieved. The gaseous refrigerant that is delivered through the further delivery line, and the refrigerant that is delivered in liquefied fashion through the capillary tube to the sample holder, are in particular the same refrigerant. The refrigerant delivered via the capillary tube and the refrigerant delivered via the further delivery line are preferably returned together via the return line.

The result of the liquefied refrigerant delivered via the capillary tube is in particular to achieve a baseline cooling effect that cools the sample holder continuously to a previously set temperature. The gaseous refrigerant that is delivered through the further delivery line results in a kind of precision control that makes possible, when necessary, a slight modification of the temperature of the sample holder. The gaseous refrigerant allows a modification of the temperature of the sample holder to be accomplished substantially more quickly and more accurately than with the liquefied refrigerant that is delivered via the capillary tube.

The further delivery line is, in particular, likewise embodied as a corrugated tube and/or a corrugated hose, so that the further delivery line can also perform the ensuing motion with little stress.

The capillary tube is fabricated in particular from a metal, so that it retains the shape that is given to it during fabrication or in which it is installed, and, upon movement of the sample holder, executes only the elastic motion possible as a result of the screw-shaped sub-region.

The capillary tube has, in particular, an inside diameter between 0.7 mm and 1 mm, preferably between 0.85 mm and 0.95 mm. This ensures that the liquefied refrigerant expands and evaporates, and thereby absorbs heat, only in the region of the sample holder, so that what is cooled is the sample holder and not already the capillary tube. This avoids icing of the capillary tube. With the aforementioned very small inside diameters it would not be possible to embody the capillary tube as a corrugated tube or corrugated hose.

The cooling unit is embodied in particular in the form of a compression-type refrigerating machine, such as those known for example from refrigerators. The compression-type refrigerating machine encompasses the compressor; the capillary tube acting as a throttle; a condensation unit that is arranged, viewed in the flow direction of the refrigerant, between the compressor and the capillary tube; and an evaporation element that is arranged, viewed in the flow direction of the refrigerant, between the capillary tube and the compressor.

The gaseous refrigerant is compressed by the compressor so that it condenses in the condensation unit, in which context the refrigerant gives up energy in the form of heat. After flowing through the capillary tube, the refrigerant expands again so that it evaporates in the evaporation element arranged downstream from the capillary tube and thereby absorbs heat. The evaporated refrigerant is then compressed again by the compressor so that it once again gives up the absorbed heat in the condensation unit.

The sample holder encompasses, in particular, an evaporation element that serves as an evaporation element of the compression-type refrigerating machine. The capillary tube opens, in particular, into this evaporation element, so that the refrigerant can expand in the region of the evaporation element before it is conveyed back to the compressor via the return line that is likewise connected to the evaporation element. The further delivery line through which the gaseous refrigerant is delivered for precision control also ends in the evaporation element. The evaporation element is embodied in particular in the form of a chamber that has a considerably larger diameter than the capillary tube.

A further aspect relates to a microtome that comprises an apparatus, previously described, for sectioning histological samples. The drive unit has in particular a handwheel, such that upon a manual actuation of the handwheel, the sample holder performs a sectioning motion and a feed motion. The sectioning motion causes the sample arranged in the sample holder to be sliced into thin sections, whereas the feed motion causes the sample holder to be moved perpendicular to the sectioning direction after a thin section has been produced, so that in the context of a stationary sectioning unit, the next thin section can be produced by a corresponding sectioning motion.

The microtome may be, in particular, a cryostat microtome.

BRIEF DESCRIPTION OF THE DRAWINGS

Further features and advantages of the invention are evident from the description below which explains the invention in further detail on the basis of exemplifying embodiments in combination with the appended Figures, in which FIG. 1 schematically depicts an apparatus for sectioning histological samples.

DETAILED DESCRIPTION OF THE INVENTION

Figure 1:
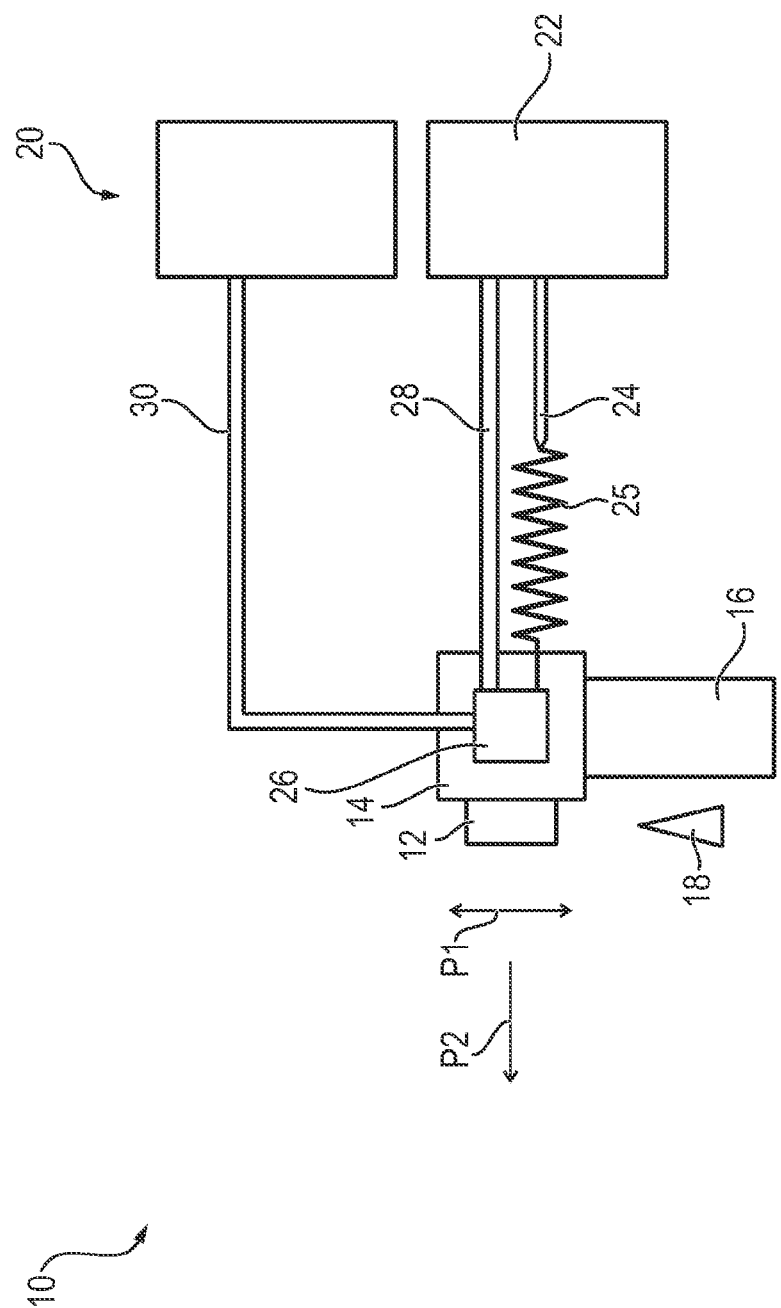

FIG. 1 schematically depicts an apparatus 10 for sectioning histological samples 12. Apparatus 10 is used in particular in microtomes.

Apparatus 10 comprises a sample holder 14 on which sample 12 is mountable for sectioning. Sample holder 14 can be moved by way of a drive unit 16 relative to a sectioning unit 18 so that sample holder 14, and thus also sample 12, performs on the one hand a sectioning motion indicated by double arrow P1, and on the other hand a feed motion P2 directed perpendicular to sectioning motion P1. By way of sectioning motion P1, sample holder 14 and thus sample 12 are moved in such a way that sample 12 is guided past a cutting edge of sectioning unit 18, and a thin section is thereby cut off from sample 12. After a thin section is cut off, a motion of sample holder 14 in feed direction P2 occurs, so that a further thin section can then be cut off from sample 12 by another execution of sectioning motion P1. For sectioning, sample holder 14 is moved approximately a distance of 60 mm, and for feeding a distance of approximately 25 mm.

Drive unit 16 comprises, in particular, a handwheel and a coupling mechanism by which the handwheel is connected to sample holder 14. Upon a manual actuation of the handwheel, the rotational motion of the handwheel is transferred via the coupling mechanism to sample holder 14 in such a way that it performs sectioning motion P1 and feed motion P2, and sample 12 is thus microtomed.

Apparatus 10 further comprises a cooling unit 20 embodied as a compression-type refrigerating machine. Cooling unit 20 encompasses a compressor 22, a condensation unit 24, a capillary tube 25, an evaporation element 26, and a return line 28. Compressor 22, condensation unit 24, capillary tube 25, evaporation element 26, and return line 28 constitute a closed circuit through which a refrigerant is passed. Ammonia, carbon dioxide, and/or hydrocarbons are used, for example, as a refrigerant.

Compressor 22 compresses the refrigerant so that it liquefies in the region of condensation unit 24 while giving up heat, in which context capillary tube 25 acts as a throttle. Once the liquefied refrigerant has flowed through capillary tube 25, the liquefied refrigerant expands in evaporation element 26, absorbing heat and thus cooling the region surrounding evaporation element 26. The evaporated and now gaseous refrigerant is returned through return line 28 back to compressor 22, so that it can once again be compressed and liquefied while giving up heat.

Evaporation element 26 is embodied in the region of sample holder 14, in particular as a part of sample holder 14, so that sample holder 14 and thus sample 12 are cooled by way of cooling unit 20.

Cooling unit 20 moreover comprises a further delivery line 30 through which a gaseous refrigerant, which is also referred to as a "heating gas," can be delivered to sample holder 14. In particular, further delivery line 30 likewise opens into evaporation element 26. The gaseous heating gas delivered via further delivery line 30 makes possible precision control of the cooling of sample holder 14 so that the latter can be easily and quickly adjusted to a preset temperature. The closed circuit of the compression-type refrigerating machine, on the other hand, results in consistent and constant cooling of sample holder 14.

Figure 2:
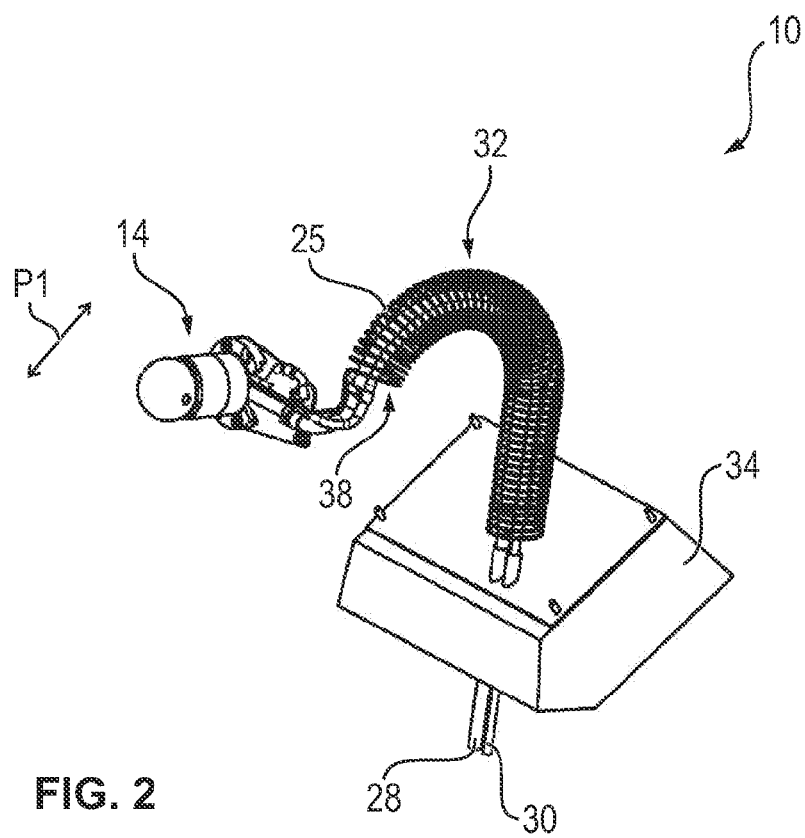
FIG. 2 is a schematic, perspective depiction of a portion of the apparatus according to FIG. 1.
Figure 3:
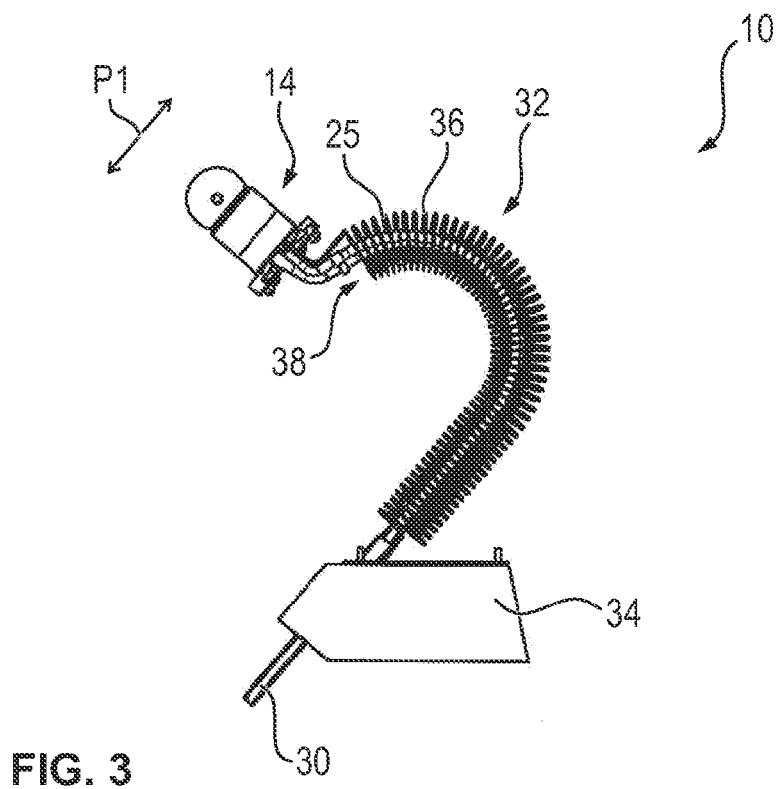
FIG. 3 is a side view of the portion of FIG. 2.

FIG. 2 is a schematic, perspective depiction of a portion of apparatus 10 according to FIG. 1. FIG. 3 is a side view of the portion according to FIG. 2. Capillary tube 25 comprises a spiral-shaped sub-region 32, at least one portion of said spiral-shaped sub-region 32 being embodied in an arc shape. This arc-shaped portion is embodied in particular in the shape of a semicircle, as is apparent from FIG. 3.

The result of the spiral-shaped configuration of sub-region 32 is that capillary tube 25 experiences less mechanical stress as sectioning motion P1 and/or feed motion P2 are executed, since spiral-shaped sub-region 32 also flexes in the context of the motion, and the mechanical stresses (in particular bending stresses) that occur are therefore low. A longer service life for capillary tube 25 is thus achieved even in a context of frequent load cycling, so that capillary tube 25 needs to be replaced less often.

The "spiral-shaped" embodiment of sub-region 32 is understood in particular to mean that this sub-region is of helical configuration, similar to a helical spring. Spiral-shaped sub-region 32 has a plurality of turns, one of which is labeled by way of example with the reference character 36. Turns 36 of spiral-shaped sub-region 32 delimit an interior space 38 through which return line 28 and further delivery line 30 are guided. The result is that on the one hand return line 28 and further delivery line 30 are protected by capillary tube 25, and on the other hand a particularly simple, compact construction is achieved. The refrigerant delivered via further delivery line 30 is, in particular, likewise transported away from sample holder 14 via return line 28.

Capillary tube 25 is embodied, in particular, from a metal and has an inside diameter in the range between 0.8 mm and 1 mm, thus reliably preventing the refrigerant compressed by compressor 22 from already expanding in the region of capillary tube 25. Effective cooling of sample holder 14 is thus achieved, and icing of capillary tube 25 is avoided.

Delivery line 28 and further delivery line 30 are embodied as corrugated hoses, so that these, too, can easily deform in the context of sectioning motion P1 and feed motion P2 and are likewise not damaged in the context of the frequent load cycling. Return line 28 and further delivery line 30 have a diameter that is substantially larger than the inside diameter of capillary tube 25.

Capillary tube 25, delivery line 28, and further delivery line 30 are, in particular, mounted on a holding element 34 of apparatus 10.

In an alternative embodiment of the invention, return line 28 and/or further delivery line 30 can also not extend through interior space 38 of capillary tube 25, but can be routed outside capillary tube 25. It is likewise alternatively possible not to use a heating gas, so that a further delivery line 30 is not necessary.

In a further alternative embodiment, spiral-shaped sub-region 32 of capillary tube 25 can also not be embodied in an arc shape but can instead extend, for example, in a straight line. It is likewise possible for spiral-shaped sub-region 32 not to be embodied helically, but instead to exhibit an irregular pitch. Turns 36 can also, in contrast to what is shown in FIGS. 2 and 3, be in contact with one another, and can thus exhibit no spacings between one another. The result of the embodiment shown in FIGS. 2 and 3, in which there is a predetermined spacing between each two adjacent turns 36, is that capillary tube 25 can deform better.

The invention is not to be limited to the specific embodiments disclosed, and modifications and other embodiments are intended to be included within the scope of the invention.

LIST OF REFERENCE NUMERALS

10 Apparatus
12 Sample
14 Sample holder
16 Drive unit
18 Sectioning unit
20 Cooling unit
22 Compressor
24 Condensation unit
25 Capillary tube
26 Evaporation unit
28 Return line
30 Delivery line
32 Spiral-shaped sub-region
34 Holding element
36 Turn
38 Interior space
P1 Sectioning motion
P2 Feed motion

What is claimed is:

1. An apparatus for sectioning histological samples, comprising:
    a sectioning unit (18) including a cutting edge configured to section the samples (12);
    a sample holder (14) on which the each sample (12) is mountable;
    a drive unit (16) configured to move the sample holder (14) relative to the sectioning unit (18) to section the sample (12) with the cutting edge; and
    a cooling unit (20) for cooling at least a sub-region of the sample holder (14), the cooling unit (20) including a compressor (22) for compressing a refrigerant, a capillary tube (25) for delivering the refrigerant to the sample holder (14), and a return line (28) for returning the refrigerant from the sample holder (14) to the compressor (22);
    wherein at least a sub-region (32) of the capillary tube (25) is spiral-shaped and configured to deform during a sectioning motion of the sample holder by the drive unit.

2. The apparatus (10) according to claim 1, wherein the spiral-shaped sub-region (32) is a helix having a constant pitch.

3. The apparatus (10) according to claim 1, wherein the spiral-shaped sub-region (32) is a spring element.

4. The apparatus (10) according to claim 1, wherein the entire capillary tube (25) is spiral-shaped.

5. The apparatus (10) according to claim 1, wherein the spiral-shaped sub-region (32) of the capillary tube (25) is curved into an arc.

6. The apparatus (10) according to claim 1, wherein a plurality of turns (36) of the spiral-shaped sub-region (32) delimit an interior space (38); and
   wherein the return line (28) extends through the interior space (38).

7. The apparatus (10) according to claim 1, wherein the return line (28) includes a corrugated tube or a corrugated hose.

8. The apparatus (10) according to claim 6, further comprising a further delivery line (30) is configured to deliver a gaseous refrigerant to the sample holder (14), the further delivery line (30) extending through the interior space (38).

9. The apparatus (10) according to claim 8, wherein the further delivery line (30) includes a corrugated tube or a corrugated hose.

10. The apparatus (10) according to claim 1, wherein the capillary tube (25) is fabricated from a metal.

11. The apparatus (10) according to claim 1, wherein at least the spiral-shaped sub-region (32) of the capillary tube (25) has an inside diameter between 0.7 mm and 1.0 mm.

12. The apparatus (10) according to claim 11, wherein at least the spiral-shaped sub-region (32) of the capillary tube (25) has an inside diameter between 0.85 mm and 0.95 mm.

13. The apparatus (10) according to claim 1, wherein the cooling unit (20) is a compression-type refrigerating machine; and
   wherein the capillary tube (25) is configured to act as a throttle of the compression-type refrigerating machine.

14. The apparatus (10) according to claim 13, wherein the sample holder (14) includes an evaporation element (26) into which the capillary tube (25) opens, the evaporation element (26) being connected to the return line (28); and
   wherein at least a part of the liquefied coolant delivered via the capillary tube (25) evaporates in the evaporation element (26).

15. The apparatus (10) according to claim 1, wherein the spiral-shape of the sub-region (32) is wound about a central axis, the sub-region being configured to deform along the central axis.

16. A microtome comprising:
   a sectioning unit (18) configured to section the samples (12);
   a sample holder (14) on which the each sample (12) is mountable;
   a drive unit (16) configured to move the sample holder (14) relative to the sectioning unit (18) to section the sample (12); and
   a cooling unit (20) for cooling at least a sub-region of the sample holder (14), the cooling unit (20) including a compressor (22) for compressing a refrigerant, a capillary tube (25) for delivering the refrigerant to the sample holder (14), and a return line (28) for returning the refrigerant from the sample holder (14) to the compressor (22);
   wherein at least a sub-region (32) of the capillary tube (25) is spiral-shaped;
   wherein the drive unit (16) includes a handwheel; and
   wherein the sample holder (14) is configured to perform a sectioning motion and a feed motion upon a manual actuation of the handwheel.

17. The microtome according to claim 16, wherein the microtome is a cryostat microtome.

18. The microtome according to claim 16, wherein the sub-region (32) of the capillary tube (25) is configured to deform during the sectioning motion.

19. The apparatus (10) according to claim 16, wherein the spiral-shape of the sub-region (32) is wound about a central axis, the sub-region being configured to deform along the central axis.

* * * * *